United States Patent [19]

Nishida et al.

[11] 4,230,697

[45] Oct. 28, 1980

[54] VIRUS-INACTIVATED HGI-GLYCOPROTEIN CAPABLE OF STIMULATING PROLIFERATION AND DIFFERENTIATION OF HUMAN GRANULOCYTE, PROCESS FOR PREPARING SAME AND LEUKOPENIA CURATIVE CONTAINING SAME

[75] Inventors: Masayuki Nishida, Osaka; Satoshi Funakoshi, Katano; Katsuhiro Ogasa, Yokohama; Morio Kuboyama; Nobuya Yanai, both of Tokyo; Muneo Yamada, Kodaira, all of Japan

[73] Assignees: Morinaga Milk Industry Co. Ltd., Tokyo; The Green Cross Corporation, Osaka, both of Japan

[21] Appl. No.: 37,515

[22] Filed: May 9, 1979

[30] Foreign Application Priority Data

Jul. 3, 1978 [JP] Japan .................................. 53-80694
Jul. 3, 1978 [JP] Japan .................................. 53-80695
Sep. 26, 1978 [JP] Japan .................................. 53-118203

[51] Int. Cl.$^3$ ...................... A61K 37/00; C07C 103/52
[52] U.S. Cl. ............................... 424/177; 260/112.5 R
[58] Field of Search .................. 424/177; 260/112.5 R

[56] References Cited

PUBLICATIONS

Bourrillon, Chem. Abstr. 75, 1971, p. 149257v.
Kinade, Jr., F.P.B.S. Abstr., p. 681.

*Primary Examiner*—Delbert R. Phillips
*Attorney, Agent, or Firm*—Cushman, Darby & Cushman

[57] ABSTRACT

A colony-stimulating factor having definite physical and chemical properties and a function of stimulating activity on human bone marrow cells to proliferate and differentiate, thereby forming granulocyte colonies, is obtained from human urine by concentrating the urine with respect to proteins contained therein by adsorption chromatography with silica gel, salting out with ammonium sulfate and other means, then removing impurities by adsorption on cation exchanger, and further purifying by ion exchanging chromatography on anion exchanger, gel filtrating chromatography with highly crosslinked gels, affinity chromatography with sugar affinitive adsorbents and electrophoresis. This substance is stable in the presence of a stabilizer such as albumin or urinary proteins, against heat-treatment of virus-inactivation and can be used as a leukopenia curative which is precluded from fear of virus-infection.

21 Claims, 4 Drawing Figures

VIRUS-INACTIVATED HGI-GLYCOPROTEIN CAPABLE OF STIMULATING PROLIFERATION AND DIFFERENTIATION OF HUMAN GRANULOCYTE, PROCESS FOR PREPARING SAME AND LEUKOPENIA CURATIVE CONTAINING SAME

This invention relates to a glycoprotein (hereinafter referred to as HGI-glycoprotein, wherein HGI means "human granulocyte inducing".) isolated from urine of normal humans, which acts on granulopoietic stem cells in human bone marrow, thereby stimulating the proliferation and differentiation of said cells to form granulocytes; and which is free from viral infections; a method for the preparation of said glycoprotein; and curatives for leukopenia containing said glycoprotein.

Although the peripheral blood of a healthy human contains 5,000 to 9,000 leukocytes per 1 mm$^3$, that of a patient of leukopenia contains below 5,000 leukocytes per 1 mm$^3$. Such a symptom of reduction in the count of leucocytes is called leukopenia. Leukopenia is associated with anomalous decrease of proliferation of bone marrow cells by some diseases, various lesions in bone marrow, exposure to radiation or administration of carcinostatic substances. For the therapy to leukopenia, there have been employed chemotherapeutics containing glycyrrhizin or cysteineglycine as active ingredient, α-mercaptopropionylglycine, or Cepharantin (a kind of alkaloids). These chemotherapeutics, however, are undesirable because of insufficient effectiveness and side effects. Accordingly, many researchers have been in progress in recent years to develop therapeutical substances for treating leukopenia which are more effective with less side effects. It was known that colony-stimulating factor (hereinafter referred to as CSF) stimulates the proliferation and differentiation of bone marrow cells. CSF acts on bone marrow cells and stimulates the proliferation and differentiation to form granulocyte or macrophage. It is an essential factor for the marrow cells, when cultured in vitro, to form granulocytic or macrophage cell aggregates (hereinafter referred to as granulocytic or macrophage colony) by simultaneous proliferation and differentiation [Ichikawa, Y., Proceedings of the National Academy of Science, Vol. 56, p. 488 (1966); Metcalf, D., Experimental Hematology, Vol. 1, p. 185 (1973)]. Since CSF induced the granulocytic and macrophage colonies from bone marrow cells, some of the researchers suggested that CSF should be regarded as separate factors that is, granulocyte inducing factor and macrophage inducing factor [Stanley E.R. et al, Journal of Experimental Medicine, Vol. 143, p. 631 (1976)]. However, in general, these factors are assayed collectively as CSF in vitro assay by mouse bone marrow cells. Many factors stimulating colony formations in vitro by mouse bone marrow cells have been isolated from various sources i.e. serum, urine, various organ extracts, and media conditioned by various tissues and cell lines, body fluid elements such as serum and urine; conditioned media of cells such as leucocyte, and tissues [Sheridan, J.W., Journal of Cell Physiology, Vol. 78, p. 451 (1971)]. CSF which acts on human bone marrow cells have been isolated from human origin i.e. various organ extracts, serum, media conditioned by tissues [Metcalf, D. and Moare, M.A.S., "Ciba Foundation Symposium 13, Haemopoietic Stem Cells", p. 157, Elsevier Excerpta Medica, Holland (1973)]. However, each CSF obtained from various organs, various cells and conditioned media thereof is not a single substance common to every sources. For instance, the molecular weight of CSF obtained from the media-conditioned by human placental cells is 30,000 dalton [Burgess, A. W. et al, Blood, Vol. 49, p. 573 (1977)], while that of CSF from human serum is 45,000 dalton [Chan, S. H. et al, British Journal of Haematology, Vol. 20, p. 329 (1971)]. Two types of CSF having molecular weights of 35,000 and less than 1,300 were isolated from media conditioned by human leukocyte [Price, G.B. et al, Blood, Vol. 42, p. 341 (1973)]. Furthermore, each CSF has different activity, some acting on either type of cells to be proliferated and differentiated to granulocyte or macropharge, others on both types of cells. Therefore, CSF's isolated from different sources are considered to be substances different from one another [Metcalf and Moore, loc. cit., (1973)].

It is also known that in human urine, there exists a type of CSF which is capable of stimulating mouse bone marrow cells to form colonies of granulocytes and macrophages in vitro [Stanley, E.R. et al., Federation Proceedings, Vol. 34, p. 2272 (1975); Stanly, E.R. and Metcalf, D., Journal of Experimental Biology and Medical Science, Vol. 47, p. 467 (1969)]. It was reported that this CSF has a molecular weight of 45,000 and stimulates the proliferation and differentiation by mouse bone marrow cells to form a macrophage dominant colony. In contrast to its stimulating effect on mouse bone marrow cells, it rarely stimulates the formation of granulocytic or macrophage colony by human bone marrow cells but consistently stimulates the formation of clusters. In this specification, with respect to human bone marrow cells, the terms "colony" and "cluster" mean cell aggregates containing 40 or more cells and 3 to less than 40 cells, respectively, in accordance with the definition of Metcalf [Metcalf, D., Experimental Hematology, Vol. 2, p. 157 (1974)].

Some of the present inventors engaged in studies on the substances having CSF activity in human urine and, as a result, found and isolated in purified state a novel HGI-glycoprotein which, quite different from the above-said known CSF, has a molecular weight of about 85,000 and acts both human and mouse bone mallow cells to form pure granulocytes colonies in vitro. Further, they succeeded in purification of the HGI-glycoprotein isolated from human urine which remarkably acts on human bone marrow cells and stimulates the proliferation and differentiation of pure granulocytes colonies (hereinafter sometimes referred to as biological activity). Further, this HGI-glycoprotein was identified, preparative method thereof with good reproducibility was developed, and uses were found, leading to the accomplishment of their invention. However, there is a fear of viral infections in the product due to most probable existence of viruses in the human urine.

An object of this invention is to provide a virus-inactivated novel CSF.

Another object of this invention is to provide a method for the preparation of this virus-inactivated novel CSF.

A further object of this invention is to provide a therapeutic agent for leukopenia, which contains the virus-inactivated novel CSF.

According to this invention there is provided a virus-inactivated glycoprotein from the human urine, which stimulates human bone marrow cells to form colonies of granulocytes and which has a molecular weight of 75,000 to 90,000 dalton as determined by gel filtration.

The HGI-glycoprotein of their invention is produced by concentrating human urine with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, eluting the adsorbed active material with a 20-100 mM saccharide solution, subjecting the eluate to preparative zone electrophoresis, eluating the active material with saline solution and recovering the active material in pure form.

Their invention is described below in details.

A typical procedures to prepare the HGI-glycoprotein of their invention is carried out in the following way. Fresh urine collected from normal humans is adjusted to pH 6-9, preferably 7-8, with dilute acid solutions or alkine solutions and then centrifuged to remove insolubles contained in the urine. The supernatant is contacted with a silicon-containing adsorbent such as silica gel, silica gel-magnesium silicate, diatomaceous earth, silica glass or bentonite and the adsorbed constituents were eluted with an alkaline solution of preferably pH 9 or higher. The alkaline solution which used for the elution is not specific, but is preferably an aqueous solution of ammonium hydroxide, sodium hydroxide or the like in a concentration of 0.3 to 1.5 M. The eluate thus obtained is adjusted to pH 7-8 with acid solution and added with a neutral salt such as, for example, ammonium sulfate to 70% saturation to salt out the active substance, whereby a crude protein fraction containing the HGI-glycoprotein is obtained.

The above crude protein fraction is re-dissolved in a small portion of an alkaline solution, freed from low molecular substances by ultrafiltration diluted with a saline buffer solution and contacted with a cation exchanger (for example, carboxymethyl dextran, carboxymethylcellulose or phosphocellulose) to remove the impurities contained in this solution. The above contact is carried out in the conditions of neutral pH, and the crude fraction of HGI-glycoprotein and the cation exchanger have been adjusted to pH 6-8 with preferably 0.01-0.15 M saline buffer solutions before the contact. Most of the HGI-glycoprotein passes through the cation exchanger without adsorption after concentration, the concentrated effluent is equilibrated with a dilute buffer solution of pH 6-8 and applied to ion-exchange chromatography with an anion exchanger, e.g. DEAE-cellulose, which has been equilibrated with the same buffer, the HGI-glycoprotein is adsorbed onto the anion exchanger. Then, the adsorbed HGI-glycoprotein is eluted by the method of so-called linear concentration gradient elution by using a 0.1-0.3 M saline solutions such as sodium chloride. The HGI-glycoprotein is eluted at a salt concentration of 0.1 M or higher but a perfect separation is difficult. The fractions of effluent at 0.1-0.3 M salt concentration are collected and, if necessary, is subjected to desalting and concentration treatments.

It is also possible that the step-wise elution with 0.1-0.3 M saline solution are applied to elute the HGI glycoprotein from the ion exchanger.

For the purpose of further purification, the combined fraction obtained above is applied to gel filtration chromatography on a highly crosslinked polymer gel having a water regain value of 10-20 ml/g such as, for example, Sephadex®G-150 or Biogel®P-100 and the active substances are developed with a 0.05-0.1 M saline buffer solution. Fractions of a relative effluent volume of 1.11 to 1.60, preferably 1.11 to 1.45, are collected, desalted and concentrated or lyophilized.

The thus obtained semi purified substances containing HGI-glycoprotein can be used as pharmaceuticals.

The relative effluent volume as herein referred to is a volume expressed by the ratio Ve/Vo (where Ve represents the volume of solvent necessary to elute the substance existing in the column and Vo represents the void volume of the column).

For further purification, the semi purified substances, obtained above is dissolved in dilute saline buffer solution containing such as, for example, a phosphate buffer solution at pH 6.0-8.0, preferably 6.0-7.0, containing 1.0-2.0 M NaCl and applied to affinity chromatography with a sugar affinitive absorbents such as, for example, concanavalin A-Sepharose 4B (supplied by Fine Chemical Laboratory), which has been equilibrated with the same buffer solution. The HGI-glycoprotein adsorbed on affinity column is eluted with a 1.0-2.0 M saline in dilute buffer containing a 20-100 mM saccharides in dilute buffer solution containing 1.0-2.0 M salt at pH 6.0-8.0, for example, saccharide is α-methyl-D-glucoside or the like at pH 6.0-8.0, preferably 6.0-7.0. The fractions containing the HGI-glycoprotein are collected and, if necessary, desalted and concentrated or lyophilized.

For still further purification of the HGI-glycoprotein by electrophoresis, the combined fraction obtained from affinity chromatography are applied to preparative zone electrophoresis using as supporting medium an acrylamide gel or agarose gel, pH 7.0-9.0, and the highly purified the HGI-glycoprotein is recovered from the supporting medium with a dilute saline solution under cooling conditions, desalted and concentrated or lyophilized.

According to their invention, it is possible to recover urokinase, callicrein and lysozyme from human urine during the course of preparing HGI-glycoprotein.

The HGI-glycoprotein thus obtained is a powder which is white or faint brown in color, is tasteless, odorless and slightly hygroscopic and has the physical and chemical properties as described below.

The physical and chemical properties were determined on sample No. 6 of Referential Example 1 (described later).

(1) MOLECULAR WEIGHT

The molecular weight of the HGI-glycoprotein was found to be about 85,000 dalton as measured by sodium dodecyl sulfate-polyacrylamide gel electrophoresis and 75,000 to 90,000 dalton as measured by gel filtration using Sephadex ® G-150. Accordingly, the most reliable molecular weight range seems to be from 75,000 to 90,000 dalton.

(2) SOLUBILITY

The solubilities of the HGI-glycoprotein in various solvents are as shown in Table 1.

TABLE 1

| Solvent | Solubility |
| --- | --- |
| Water | Soluble |
| Ethyl alcohol | Insoluble |
| Acetone | Insoluble |
| Chloroform | Slightly soluble |
| 1 M Sodium chloride solution | Soluble |
| 10% Sucrose solution | Soluble |

Beside, it is easily soluble in a dilute saline solution such as, for example, a dilute phosphate solution or a dilute trisaminomethane solution. It is also soluble in a dilute saline solution in the pH range from 1 to 12.

(3) pH

The pH of a 1% aqueous solution of HGI-glycoprotein is 5.0 to 6.0, that is, in the acidic range.

(4) SPECIFIC OPTICAL ROTATION.

The optical rotation was measured on a 0.25% aqueous solution of HGI-glycoprotein at 20° C. The specific optical rotation $[\alpha]_D^{20}$ was found to be in the range of $0 \pm 40$.

(5) INFRARED ABSORPTION SPECTRUM.

Figure 1:
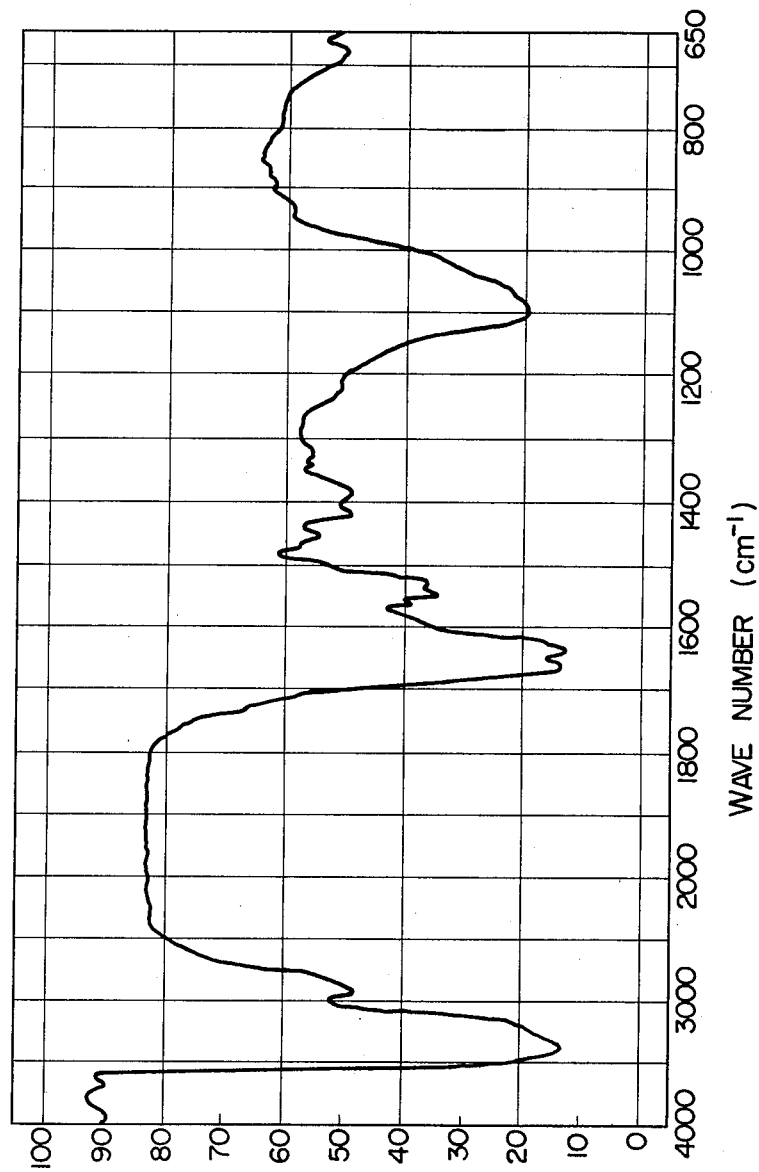
FIG. 1 represents infrared absorption spectrum of the HGI-glycoprotein.

The infrared absorption spectrum of HGI-glycoprotein as measured by the method of KBr pellets is as shown in FIG. 1. The characteristic absorption bands are as shown in Table 2.

TABLE 2

| Absorption wave number (cm$^{-1}$) | Degree of absorption | Remarks |
| --- | --- | --- |
| 3600-3200 | Strong | The broad absorption band seems to be originated from the $v$—OH groups forming various degrees of hydrogen bands. |
| 1700-1600 | Strong | The broad absorption band seems to be originated from —CO . NH— bonds of protein fragment. |
| 1550 | Medium | |
| 1430-1380 | Medium | |
| 1150-1000 | Medium | The braod absorption band seems to be originated from —C—O—C— bonds of polysaccharide fragment. |

(6) ISOELECTRIC POINT

The isoelectric point of HGI-glycoprotein is pH $4.7 \pm 0.2$, as measured by polyacrylamide gel isoelectric focussing.

(7) Color reaction

Various color reactions were examined on HGI-glycoprotein dissolved in water. The results obtained are as shown in Table 3.

TABLE 3

| Color reactions | Developed color | Remarks |
| --- | --- | --- |
| Lowry-Folin's reaction | Blue | Peptide bonds |
| Ninhydrin reaction (hydrolyzed with 6N HCl at 110° C. for 22 hours) | Violet | α-amino acids |
| α-Naphthol-sulfuric acid reaction (Molisch's reaction) | Violet | Saccharides |
| Indole-sulfuric acid reaction (Dische's reaction) | Brown | " |
| Anthrone-sulfuric acid reaction | Dark green | " |
| Phenol-sulfuric acid reaction | Brown | " |

(8) THERMOSTABILITY

On heating a 1% aqueous solution of HGI-glycoprotein at $60 \pm 0.5°$ C. for 30 minutes, the CSF activity was no more detectable.

(9) AMINO ACID COMPOSITION OF THE PROTEIN FRAGMENT.

HGI-glycoprotein was hydrolyzed with 1 N hydrochloric acid at 110° C. and the amino acid composition of the protein fragment was determined by means of an amino acid autoanalyzer to obtain the results as shown in Table 4.

TABLE 4

| Amino acid | Weight % | Mole (mM) |
| --- | --- | --- |
| Proline | 3.2 | 0.392 |
| Aspartic acid | 9.8 | 1.038 |
| Threonine | 2.8 | 0.331 |
| Serine | 11.9 | 1.596 |
| Glutamic acid | 13.8 | 1.322 |
| Glycine | 11.0 | 2.066 |
| Alanine | 7.3 | 1.155 |
| Valine | 6.4 | 0.771 |
| Methionine | 2.5 | 0.236 |
| Isoleucine | 2.5 | 0.269 |
| Leucine | 7.0 | 0.753 |
| Tyrosine | 5.8 | 0.451 |
| Phenylalanine | 12.8 | 1.050 |
| Lysine | 2.2 | 0.212 |
| Histidine | 1.0 | 0.091 |
| Trypophan | trace | — |
| Arginine | trace | — |
| Ammonium | 0.5 | — |

It is seen from Table 4 that the protein fragment of the HGI-glycoprotein is composed of 17 amino acids of which acidic and neutral amino acids dominante, while basic amino acids are minor constituents. It is also one of the characteristics that over 70% of the total amino acids are linear amino acids including aspartic acid, threonine, serine, glutamic acid, glycine, alanine, valine and leucine.

(10) ELECTROPHORESIS

Figure 2:
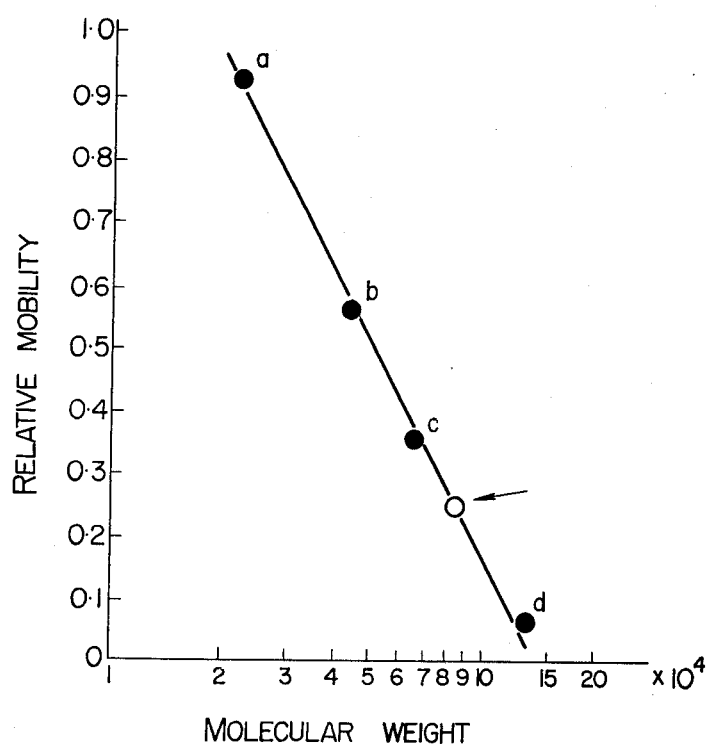
FIG. 2 shows the correlation between the relative mobility in electrophoresis and the molecular weight.

By following the Laemuli's method [Nature, Vol. 227, p. 680 (1970)] and using a sodium dodecyl sulfate-polyacrylamide gel, the HGI-glycoprotein which shows single band at a position of relative mobility of 0.25, trypsin inhibitor (molecular weight 21,500), ovalbumin (molecular weight 43,000), human serum albumin monomer (molecular weight 65,000) and human serum albumin dimer (molecular weight 130,000) were simultaneously electrophored. From the mobilities of the substances having known molecular weights and that of the HGI-glycoprotein, the molecular weight of the latter was found to be about 85,000 (FIG. 2). In FIG. 2, a, b, c and d represent trypsin inhibitor, ovalbumin, human serum albumin monomer, and human serum albumin dimer, respectively, and the arrow represents the HGI-glycoprotein.

(11) ULTRAVIOLET ABSORPTION SPECTRUM.

Figure 3:
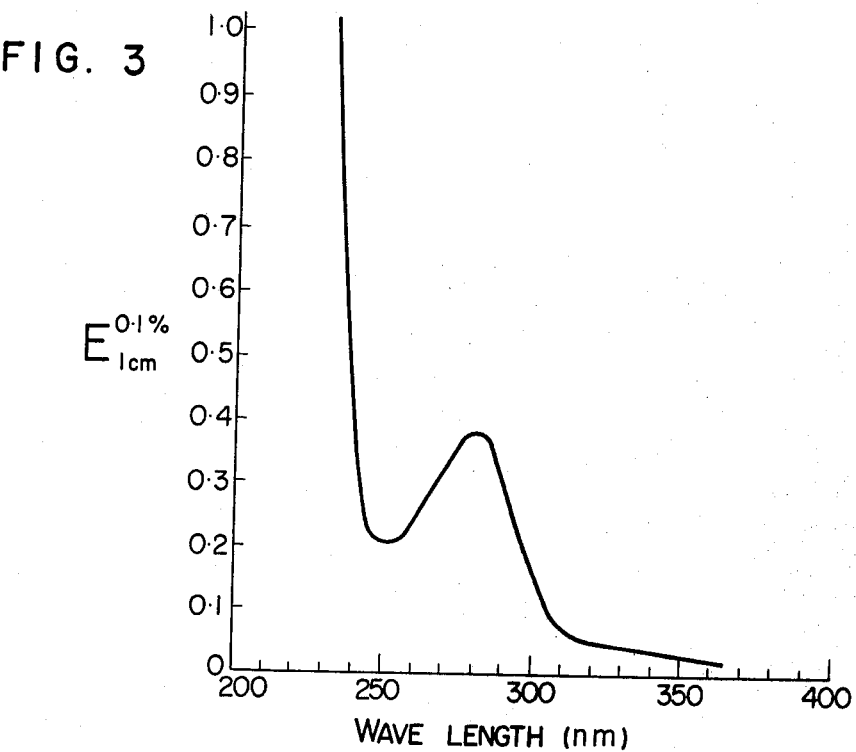
FIG. 3 shows ultraviolet absorption spectrum of the HGI-glycoprotein.

Ultraviolet absorption spectrum of the HGI-glycoprotein, as measured on a 0.1% aqueous solution in a 1 cm silica cell, is shown in FIG. 3. It shows the maximum absorption at 280 nm and terminal absorption in the wave length region shorter than 250 nm. The optical density $E_{1cm}^{1\%}$ at 280 nm is 3.8.

(12) Sugar composition of polysaccharide fragment.

Neutral sugars were determined by the phenolsulfuric acid reaction, sialic acids by the Warren's thiobarbital method [Journal of Biological Chemistry, Vol. 234, p. 1971 (1959)], and amino sugars by the Elson-Morgan method [Biochemical Journal, Vol. 27, p. 1824 (1933)]. The weight of neutral sugars were expressed in terms of glucose. The results were as follows: neutral sugars: 10.0–13.0%; sialic acids: 3.0–7.0%; amino sugars: less than 1.0%; total sugar: 13.0–20.0%.

(13) Composition ratio of protein and polysaccharide.

The protein content of HGI-glycoprotein is 75–85%, as determined by the semi-micro Kjeldahl method. The total sugar content is 13.0–20.0%, as described above.

(14) Elementary analysis

The results of elementary analysis of HGI-glycoprotein are as follows: C, 42.3–47.3%; H, 5.7–7.8%; N, 9.6–14.3%, O, 34.4–39.4%; S, less than 0.2%.

The HGI-glycoprotein of the above physical and chemical characteristics has a function of stimmulating the proliferation and differentiation of both human and mouse granulocytes as seen from Test 1 (described later) and shows no acute toxicity as evidenced by Test 4 (described later). Further, as is apparent from the resutls of Test 3 (described later), it can be utilized as leukopenia chemotherapeutics.

The HGI-glycoprotein prepared from human urine by the aforesaid procedure is aseptically lyophilized in vials and hermetically sealed. It is also possible, prior to the lyophilization, to add to the HGI-glycoprotein an aqueous solution containing human serum albumin as stabilizer and an amino acid or a saccharide as solubilizing aid; the resulting solution is sterilized by membrane filtration and then aseptically lyophilized. Before using, the vial is unsealed and the HGI-glycoprotein is dissolved by adding sterilized physiological saline solution, sterile water or a sterile isotonic solution. The resulting solution is administered to the patient with leukopenia by intravenous, intramuscular or subcutaneous injection.

From the results of Tests 1 and 2 (described later), the effective dose is 0.75 mg or more, preferably 0.75 to 2.24 mg, per day per kg of body weight. Semipurified products, prepared on a large scale, having a specific biological activity of 35,000 units/mg or more such as those containing HGI-glycoprotein corresponding to sample No. 4 and No. 5 of Referential Example 1 (described later) may also be used as pharmaceuticals.

The effect of HGI-glycoprotein on the proliferation and differentiation of granulocytes is described below in detail.

TEST 1

Stimulating effects on proliferation and differentiation of mouse and human granulocytes in vitro.

Figure 4:
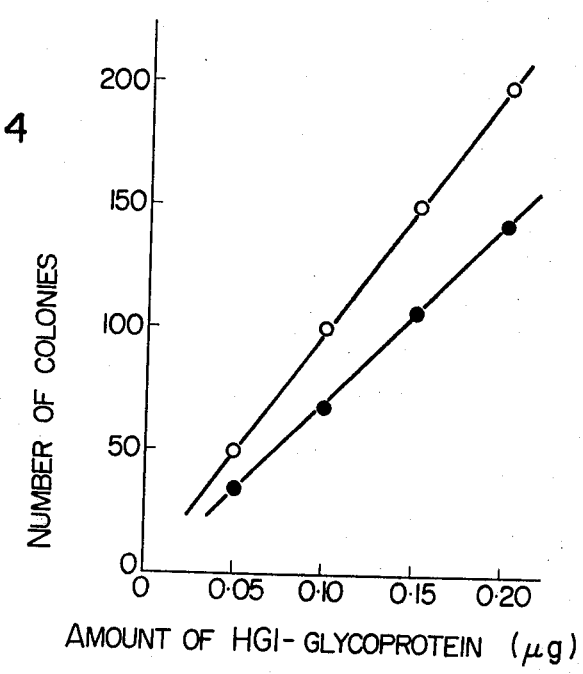
FIG. 4 shows the relationship between the addition amount of the HGI-glycoprotein and the number of colonies developed in vitro assay.

In each plastic Petri dish, 35 mm in diameter, was placed 1 ml of McCoy's 5 A medium containing 0.05, 0.1, 0.15 or 0.2 μg of HGI-glycoprotein (sample No. 6 of Referential Example 1), 20% of fetal calf serum, 0.3% of agar and $7.5 \times 10^4$ mouse bone marrow cells or $25 \times 10^4$ bone marrow cells of normals or patients with iron-deficiency anemia. The medium in the Petri dish was incubated in a humidified 5% $CO_2$ atmosphere at 37° C. for 7 to 9 days. The difference in the number of introduced cells between the mouse and man was due to a greater number of stem cells in the case of mouse. After incubation, discrete colonies containing more than 50 cells for mouse or more than 40 cells for human were counted with an inverted microscope. For morphologic analysis of colonies, some of them were picked up with microhematocrit tubes and stained with 0.6% orcein in 40% acetic acid. The results obtained were as shown in FIG. 4. FIG. 4 shows the interrelationship between the dose of HGI-glycoprotein and the number of colonies which were formed in vitro. In FIG. 4, —○—○—pertains to the mouse bone marrow cell and —●—●—to the human bone marrow cell.

As is apparent from FIG. 4, HGI-glycoprotein stimmulates the proliferation and differentiation of bone marrow cells of mouse and man, thereby forming colonies and there are dose-response relationships between HGI-glycoprotein and formed colony numbers.

On the morphologic analysis of the cells formed colonies, it was observed that these cells were all mature granulocytes.

As described above, HGI-glycoprotein acts on both human and mouse bone marrow cells to form colonies of granulocytes, the number of colonies being proportional to the dose of HGI-glycoprotein, and there is a definite relationship in the formation of colonies of bone marrow cells between mouse and humans. Therefore, in all of the following experiments, only mouse bone marrow cells were employed.

TEST 2

Stimulating effects on proliferation and differentiation of granulocyte in vivo.

Sixty $C_{57}BL$ male mice (20 g of average body weight) were divided at random into 6 groups of each 10 members. One group, which served as control, was subcutaneously administered with 0.04 mg/mouse of human serum albumin dissolved in 0.2 ml of sterile normal saline solution, once a day, for 3 consecutive days. The remaining 5 experimental groups, i.e. 1st, 2nd, 3rd, 4th and 5th group, were subcutaneously administered respectively with 0.005, 0.01, 0.02, 0.03 and 0.04 mg/mouse of HGI-glycoprotein (sample No. 6 of Referential Example 1 described later) each dissolved in 0.2 ml of sterile normal saline solution, once a day, for 3 consecutive days.

Blood samples were collected from the vena coccygea of each mouse before administration and 2, 4, 6, 8 and 10 days after administration. The leukocytes of each blood sample were stained with 1% gentiana violet solution and leukocyte numbers were counted with a Bürker-Türk counting chamber.

Further, each blood sample was smeared on a slide glass, stained with Wright-Giemsa solution, and the proportion of granulocytes in leukocytes was measured under a microscope.

The number of granulocytes was calculated by the following formula:

(number of leukocytes in 1 mm$^3$) × (proportion of granulocytes in leukocytes) = number of granulocytes in 1 mm$^3$.

The results obtained were as shown in Table 5.

TABLE 5

| | Group | | | | | |
|---|---|---|---|---|---|---|
| | Control | 1st | 2nd | 3rd | 4th | 5th |
| | | | | Dose (mg) | | |
| Days | 0 | 0.005 | 0.01 | 0.02 | 0.03 | 0.04 |
| 0 | 450 | 452 | 455 | 450 | 448 | 445 |
| 2 | 380 | 420 | 550 | 600 | 775 | 800 |
| 4 | 372 | 390 | 800 | 1100 | 1400 | 1420 |
| 6 | 380 | 395 | 1100 | 1800 | 2200 | 2100 |
| 8 | 410 | 400 | 620 | 750 | 980 | 971 |
| 10 | 430 | 410 | 470 | 460 | 465 | 480 |

Note:
Each numerical value represents mean number of granulocytes per mm$^3$ for 10 mice.

As shown in Table 5, it is indicated that the peripheral granulocyte counts of the experimental groups administrated with 0.01–0.04 mg/mouse of the HGI-glycoprotein began to increase after 2 days of administration and reached to 3–6 times of the count of control groups after 6 days.

The granulocyte counts decreased and returned to the normal level at 10 days. When the daily dose was increased to excess 0.04 mg, there were no significant increase of granulocytes corresponding to increasing dose of the HGI-glycoprotein.

These results suggested that the granulocytosis can be sufficiently produced by daily injection of 0.01 mg or more, preferably 0.01–0.03 mg, of HGI-glycoprotein to a mouse (mean body weight is approximately 20 g). However, since the stimulating effect of HGI-glycoprotein on mouse bone marrow cells in vitro is an average of about 1.5 times higher than the effect on human bone marrow cells (Test 1), the effective dose for man is presumed to be 1.5 times as high as that for mouse determined in vivo in Test 2. Accordingly, the effective daily dose per kg of body weight for man is estimated as 0.75 mg or more, preferably 0.75 to 2.24 mg.

TEST 3

Protective effect of HGI-glycoprotein on leukopenia caused by carcinostatic substances.

Thirty C$_{57}$BL male mice, 4–5 weeks old, were divided at random into 3 groups of 10 members. The control group was administered by intraperitoneal injection with 30 mg/kg body weight (equivalent to 1/10 LD$_{50}$) of cytosine-D-arabinosine dissolved in 0.2 ml of sterile normal saline solution, once a day, for 14 consecutive days. In addition, 0.2 ml/mouse of sterile normal saline solution was subcutaneously administered once a day for 14 consecutive days. Another group (HGI-leucoprotein administered group) was administered with cytosine-D-arabinoside in the same manner as in the control group. In addition, 0.03 mg/mouse of HGI-glycoprotein (sample No. 6 of Referential Example 1 described later) was subcutaneously administered once a day for 14 consecutive days. The remaining group (Cepharantine administered group) was administered with cytosine-D-arabinoside in the same manner as in the control group and further administered subcutaneously with 0.3 mg/mouse of Cepharantine (Kaken Pharmaceuticals Co.; conventionally employed for leukopenia) dissolved in 0.2 ml of sterile normal saline solution, once a day for 14 consecutive days.

Blood samples were collected from the vena coccygea of each mouse before administration and 2, 4, 6, 8, 10, 12 and 14 days after administration. The number of leukocytes was measured as in Test 2 and the percentage decrease (decrement) in number of leukocytes after administration was obtained by assuming the count before administration as 100. The results were shown in Table 6.

TABLE 6

| Group | Control | | HGI-glycoprotein administered | | Cepharantine administered | |
|---|---|---|---|---|---|---|
| Days after administration | Leucocyte count (× 10$^2$/mm$^3$) | Decrement (%) | leucocyte count (× 10$^2$/mm$^3$) | Decrement (%) | Leucocyte count (× 10$^2$/mm$^3$) | Decrement (%) |
| Before administration | 150 | 100 | 150 | 100 | 150 | 100 |
| 2 | 130 | 86.6 | 120 | 80.0 | 125 | 83.3 |
| 4 | 125 | 83.3 | 125 | 83.3 | 120 | 80.0 |
| 6 | 120 | 80.0 | 130 | 86.6 | 120 | 80.0 |
| 8 | 110 | 73.3 | 120 | 80.0 | 110 | 73.3 |
| 10 | 95 | 63.3 | 120 | 80.0 | 100 | 66.6 |
| 12 | 80 | 53.3 | 115 | 76.6 | 105 | 70.0 |
| 14 | 70 | 46.6 | 110 | 73.3 | 95 | 63.3 |

Note:
Each numerical value is an average for 10 mice.

As compared with the control group, the HGI-glycoprotein administered group showed a marked preventive effect on the reduction in leucocyte count after ten days from the beginning of the HGI-glycoprotein administration, the effect being comparable or superior to that of Cepharantine. On the 14th day from the beginning of administration, the leukocyte count of the control group was reduced to 46.6%, whereas that of the HGI-glycoprotein administered group was 73.3%, the decrement beging less than that of the Cepharantine administered group. Therefore, it is presumable that the HGI-glycoprotein will be effective for the therapy of human leukopenia.

It was also confirmed that the HGI-glycoprotein is also effective when other carcinostatic substances such as, for example, 5-fluorouracil and daunomycin were administered which have been known to cause reduction in leukocyte count similarly to cytosine-D-arabinosid. No preventive effect on the reduction in leukocyte count was observed when human serum albumin was examined in the same manner as described above.

TEST 4

Acute toxicity of the HGI-glycoprotein.

The acute toxicity of HGI-glycoprotein prepared in Referential Example 1 (samples No. 4 and No. 6) was tested on $C_{57}BL$ male mice by the method of Lichied and Wilcoxon [Journal of Pharmacology and Experimental Therapeutics, Vol. 90, p. 99 (1949)]. No fatal case was found when 4,000 mg/kg body weight was administered intraperitoneally or 2,000 mg/kg body weight was administered intravenously. Consequently, estimation of $LD_{50}$ was practically impossible, $LD_{50}$ of subcutaneous injection was above 4,000 mg/kg body weight and $LD_{50}$ of intravenous injection was above 2,000 mg/kg of body weight.

REFERENTIAL EXAMPLE 1

Four hundred liters of fresh urine collected from normal humans was adjusted to pH 8 with 10% sodium hydroxide and centrifuged by menas of a continuous centrifugation at 15,000 G at 0° C. to remove insolubles. The supernatant was adjusted to pH 7 with 10% hydrochloric acid and passed through a silica gel column (10×80 cm). The substances adsorbed or the silica gel were eluted with 40 liters of 5% ammonium solution. The eluted solution was adjusted to pH 7.5 with 1 N sulfuric acid, and added with ammonium sulfate to 70% saturation, and left standing at 0° C. for overnight. The precipitate was collected by filtration, dissolved in 2 liters of 5% ammonium solution, placed in cellophane tubes (Visking Co.) and dialyzed against 0.05 M phosphate buffer solution (pH 6.5). The dialyzed solution was mess up to 10 liters with the same buffer solution and passed through the CM Sephadex C-50 ® ion exchange column (40×40 cm) which had been equilibrated with 0.05 M phosphate buffer solution (pH 6.5), to adsorb the contaminants on the ion exchange resin. Ten liters of the effluent solution was concentrated by means of DIAFLO hollow fiber ultrafiltration apparatus (Amicon DC-30, U.S.A, molar weight cut off approximetly 10,000). The concentrated solution was dialyzed against 0.1 M tris-HCl buffer (pH 7.0) at 5° C. for overnight. The dialyzed solution was made up to one liter with the same buffer solution (the resulting solution is referred to as sample No. 1).

The above solution was passed through the DEAE cellulose column (4.0×40 cm) which had been equilibrated with 0.1 tris-HCl buffer (pH 7.0) and washed the column with sufficient volume of 0.1 M tris-HCl buffer (pH 7.0). The loaded column was carried out the step wise elution with 0.1 M tris-HCl buffer solution (pH 7.0) containing 0.3 M sodium chloride. The fractions capable of effecting proliferation and differention of granulocyte, as tested in the same manner as in Test 1, were collected and dialized against 0.1 M tris-HCl buffer (pH 7.0) (this solution is referred to as sample No. 2).

The dialized solution was again passed through DEAE cellulose column (4.0×40 cm) which had been equilibrated with 0.1 M tris-HCl buffer (pH 7.0) and the loaded column was carried out the linear concentration gradient with elution sodium chloride (0 to 0.3 M). The active fractions were collected and added with ammonium sulfate to 70% saturation. The precipitates were collected by centrifugation and dissolved in a small volume of 0.1 M tris-HCl buffer (pH 7.0) and dialized against the same buffer solution (this dialized solution is referred to as sample No. 3).

Twenty milliliters of the dialized solution was applied to Sephadex G-150 column (4.0×60 cm) which had been equilibrated with 0.1 M tris-HCl buffer (pH 7.0) and the effluent fractions obtained at Ve/Vo ratios of 1.11–1.45 were collected. The combined fraction was thoroughly dialized against distilled water at 5° C. and the dialized solution was lyophilized to obtain about 500 mg of a powder (this semi-purified HGI-glycoprotein is referred to as sample No. 4).

Two hundred milligrams of the semi-purified HGI-glycoprotein was dissolved in 0.02 M phosphate buffer (pH 7.0) containing 1.0 M sodium chloride and passed through 100 ml of concanavalin A-Sepharose 4B affinity column which had been equilibrated with the same buffer. After thorough washing of the column with the same buffer, the HGI-glycoprotein was eluted with 0.02 M phosphate buffer (pH 7.0) containing 50 mM α-methyl-D-glucoside and 1.0 M sodium chloride. The fractions which is capable of effecting proliferation and differentiation of granulocyte in vitro were collected and dialized against distilled water. The dialized solution was lyophilized (this is referred to as sample No. 5).

About 50 mg of the above lyophilized powder was dissolved in 1 ml of 0.125 M tris-glycine buffer (pH 6.8) containing 10% glycerine. The resulting solution was electrophored at 10 mA under cooling by means of a preparative electrophoresis apparatus (Type Fuji Kabara II of Fuji Riken Co., Japan) employing 8% acrylamide gel (pH 8.9; 20 mm×25 mm). The fraction with a relative mobility of 0.46 was recovered with 0.025 M tris-glycine buffer (pH 8.3) and was dialized against distilled water. The dialized solution was lyophilized to obtain about 10 mg of the HGI-glycoprotein (which is referred to as sample No. 6).

The samples No. 1 to No. 6 obtained in various stages of preparation were tested for the proliferation and differentiation effect on both human and mouse bone marrow cells in a manner similar to that in Test 1. The HGI-glycoprotein or a fraction containing same was added to the medium in an amount necessary to form 200 colonies per dish. The specific activity was calculated by the following formula, wherein one unit corresponds to one colony formed:

Specific activity (units/mg) = 
$$\frac{\text{Number of colonies formed (units)}}{\text{protein content (mg) of assayed sample}}$$

The results were as shown in Table 7.

TABLE 7

| | Mouse bone marrow cell assy | | Human bone marrow cell assy | |
|---|---|---|---|---|
| Sample | Specific activity (units/mg) | Fold purification | Specific activity (units/mg) | Fold purification |
| No. 1 | 260 | 1 | 160 | 1 |
| No. 2 | 4,500 | 17.3 | 2,200 | 13.8 |
| No. 3 | 11,000 | 42.3 | 5,500 | 34.4 |
| No. 4 | 57,000 | 219.2 | 35,000 | 218.8 |
| No. 5 | 210,000 | 807.7 | 180,000 | 1125.0 |
| No. 6 | 1,000,000 | 3846.1 | 670,000 | 4187.5 |

REFERENTIAL EXAMPLE 2

To 100 mg of HGI-glycoprotein powder (sample No. 6) obtained in the same way as in Referential Example 1, was added 100 ml of an aqueous solution containing 5% human serum albumin (Sigma Co., USA) and 1% glycine (Wako Pure Chemicals Co., Japan). The resulting solution was sterilized by Millipore filtration system (Millipore Co., USA) provided with membrane filters of 0.45µ pore size. The sterilized solution was aseptically filled, in 1 ml portions, in vials which had been sterlized by heating at 180° C. for 2 hours. After lyophilization, the vials were hermetically sealed. In this way, ther were obtained 95 vials of a therapeutic agent for leukopenia, each vial containing 1 mg of HGI-glycoprotein.

REFERENTIAL EXAMPLE 3

In a same manner to that in Referential Example 1, one liter of a concentrated solution containing HGI-glycoprotein, which was analogous to sample No. 1, was prepared from 1,000 liters of fresh urine collected from normal humans. To this concentrated solution was diluted with 10 liters of 0.1 M tris-HCl buffer (pH 7.0). After thorough stirring, the diluted solution was reconcentrated to about one-tenth of the original volume by use of DIAFLO ® hollow fiber ultrafiltration apparatus. The concentrated solution was added 5 liters of 0.1 M tris-HCl buffer (pH 7.0) and 5 liters of DEAE cellulose suspension containing 300 g on dry basis of DEAE cellulose, which had been equilibrated with 0.1 M tirs-HCl buffer (pH 7.0). The mixture was stirred for 30 minutes, stand for 10 minutes and filtrated under vacuum on a Buchner funnel to collect the DEAE cellulose. The collected DEAE cellulose was washed with 10 liters of 0.1 M tris-HCl buffer (pH 7.0) and recollected by filtration as same as above. The DEAE cellulose was further washed with 10 liters of 0.1 M tris-HCl buffer (pH 7.0) containing 0.05 M sodium chloride and recollected by same manner as above. The DEAE cellulose thus treated, was added with 10 liters of 0.1 M tris-HCl buffer (pH 7.0) containing 0.3 M sodium chloride and stirred to free the HGI-glycoprotein from the DEAE cellulose. The mixture was filtrated by same manner as above and filtrated solution was collected. The filtrated solution was desalted by DIAFLO hollow fiber ultrafiltration. The desalted solution was lyophilized to collect about 15 g of a powder. The powder was dissolved in 150 ml of distilled water and applied to Sephadex G-150 (column (6.0×80 cm) which had been quilibrated with 0.1 M tris-HCl buffer (pH 7.0). The fractions corresponding to Ve/Vo ratios of 1.11–1.60 were collected. The combined fraction was thoroughly dialized against distilled water. The dialized solution was concentrated by DIAFLO hollow fiber concentration apparatus (Type DC-2) to about 100 ml of a concentrate containing about 3 g of crude HGI-glycoprotein. The concentrated solution was added with 1 g of glycine (Wako Pure Chemicals Co.) and 5 g of serum albumin (Sigma Co.). The resulting solution was sterilized by filtration in the same manner as in Referential Example 1 and aseptically filled, in 2.5 ml portions, in vials. After aseptic lyophilization, the vials were hermetically sealed. Thus, there were obtained 40 vials of a therapeutic agent for leukopenia, each vial containing about 3.8 mg of the HGI-glycoprotein.

On the view of clinical applications of the HGI-glycoprotein, it is very important that the elimination of the pathogenic viruses which are contained in urine and capable of causing some hepatitis and endemic diseases from a medicine prepared with the HGI-glycoprotein as well as other medicines constitutes with human blood elements. When a medicine produced from human urine is administered on patients without prior treatment for removing or inactivating the viruses, there is always a hazard of viral infections. And the similar problem is taken account of the HGI-glycoprotein.

In order to avoid the hazard of viral infections caused by viral contamination, the preliminary inspections have to carried out in urine materials to exclude the viral contaminated ones from the starting materials. Although such a practice has been proved to be effective to a certain extent in preventing the viral infection, it is impossible to adopt such a means in a factory where the urine material collected from several tens of thousands persons is treated at a time.

On the other hand, human serum protein agents prepared from human plasma for medical supplies also involved the problem of viral infection. Since the time when it was found that the viral infection caused by serum albumin agents can be prevented by the heat-treatment at 60° C. for 10 hours, without denaturation, all serum albumin agents have undergone similar heat treatment and been clinically used safely. Therefor these heat treatments are utilized also in the production of other human serum protein agents.

In order to be able to apply the heat treatment at 60° C. for 10 hours, to medicenes constitutes being treated must be stable under the conditions. For this purpose, various stabilizers have been found. Among those substances which cannot withstand such a heat treatment, some of them can be heat resistant in the presence of a stabilizer. For the purpose of stabilizing human serum proteins against heat treatments, some kinds of amino acids or saccharides are used at the physiologically isotonic concentration or lower. Although it is desirable for the HGI-glycoprotein to inactivate viruses by heat treatment, the biological activity of the HGI-glycoprotein is lost by the heat treatment at 60° C. for 10 hours as described.

The present inventors have found that under the following conditions the HGI-glycoprotein in aqueous solution is improved in heat stability and becomes resistant to the above-said heat treatment without deterioration in its characteristic properties. Namely, the HGI-glycoprotein is stable to heat treatment at pH 5–9 when the albumin is present in the solution at 2% above or when the concentration of the HGI-glycoprotein in the solution is as high as 70 mg/ml or higher, or when human urinary proteins are present in a concentration of 70 mg/ml or higher.

Thus, the present invention provides the HGI-glycoprotein which has applid the inactivation treatment for the viruses contaminated in the HGI-glycoprotein. The inactivation treatment for the viruses in this invention comprises heating the queous solution of the HGI-glycoprotein, which had been stabilized against heat according to the following manners, at 50° C. to 70° C., preferably 55° to 65° C. for 8 to 30 hours, preferably 8 to 12 hours, and at a pH of 5 to 9.

When the albumin is used as the stabilizer, the purification degree of the HGI-glycoprotein contained in the aqueous solution is not critical but the HGI-glycoprotein fractions of the purity level corresponding to those of samples No. 4 to No. 6 in Referential Example 1 are preferred. The concentration of the HGI-glycoprotein in the aqueous solution to be heat-treated is 0.1% (W/V%, that is, number of weight units in 100 volume units; the same applies hereinafter with respect to aqueous solution) or higher, preferably 0.5 to 15%.

The aqueous solution is adjusted to pH 5–9, preferably 6–8, by the addition of an acid or alkali solution, preferably a buffer solution. The albumin preparation used in the invention can be of the human serum origin or human placenta origin, both of which have been preferably purified for medical usages and have a purity of 80% or more, as assayed by electrophoresis. The amount of albumin to be added to the HGI-glycoprotein containing aqueous solution is 2.0% or more, preferably 10 to 20%. The upper limit of the amount of the albumin added is not particularly limited and the suitable amount depends on the allowable proportion of albumin in the final product.

The use of the albumin prepared from human origins in stabilizing the HGI-glycoprotein against heat precludes the danger of contamination of the final product with antigenic substances and permits effective stabilization of the HGI-glycoprotein against heating. In addition, since albumin ensures the stability of glycoprotein preparations in preservation, the removal of albumin after heat treatment is unnecessary so long as a suitable amount is used in heat treatment. Therefore, the heat treatment according to this invention is an efficient step to be included in the process for preparing the HGI-glycoprotein and certainly contributes to the industrial production process including a virus inactivation step.

TEST 5

The effect of heat treatment in the presence of albumin on the virus infectivity was examined using various viruses having a possibility of contaminating the HGI-glycoprotein preparations.

The HGI-glycoprotein prepared in the same manner as sample No. 4 of Referential Example 1 was dissolved in water to prepare a 100 mg/ml solution. These solutions were inoculated with 0.2 ml of a virus suspension (having a virus infection does of $1\times10^5-1\times10^6$/0.2 ml as measured by the method described later) of smallpox virus, mumps virus, measles virus, herpesvirus, chikungunya virus, Japanese encephalitis virus, rubella virus, poliovirus, coxsackievirus, or echovirus followed by 0, 20, 100 or 200 mg/ml of human serum albumin (Sigma Chemical Co.). The resulting solution was adjusted to pH 7.0 with 0.1 M tris-HCl buffer, then heated at 60° C. for 10 hours, thereafter cooled immediately in ice cold water, desalted, sterilized by membrane filtration and lyophilized to obtain a powder. The biological activity and virus infection were assayed by the following methods and compared with those before heat treatment.

The assay of biological activity was performed by observing as parameter the colony formation by mouse bone marrow cells in vitro. In each plastic Petri dish, 35 mm in diameter was placed 1.0 ml of the supplemented Mc Coy's 5A medium containing 20% of fetal calf serum, 10% (0.1 ml) sample, 0.3% of agar, $7.5\times10^4$ mouse bone marrow cells and 10% (0.1 ml) of sample, the concentration of each sample having been adjusted to the equal. After 7 days incubation in a humidified 5% $CO_2$ atmosphere, discrete colonies containing more than 50 cells were counted with an inverted microscope. The ratio (in %) of the number of colonies formed after heat treatment to that before heat treatment was referred to as recovery of biological activity.

The virus infective dose was determined in the following way. Samllpox virus was successively transplanted in HeLa cells and the focus forming unit [Virology, Vol. 36, pp. 174–179 (1968)] was determined with the same cell. Successive transplant of mumps virus, measles virus and Japanese encephalitis virus were carried out with VERO cells and that of poliovirus, coxsackievirus and echovirus with HeLa cells. Infectivity of each virus was assayed by determining 50% tissue culture infective dose [National Institute of Health, Japan (Ed.), "Experimental Virology", Maruzen Co., Tokyo, 1967] using the cytopathic effect as indicator. The observation period was 10 days.

Herpesvirus and chikungunya virus were successively transplanted in FL cells and VERO cells, respectively, and the plaque forming unit ("Experimental Virology", loc. cit.) were determined.

Rubella virus was successively transplanted in BHK-21 cells and the plaque forming unit were determined with VERO cells.

The results obtained were as shown in Table 8.

TABLE 8

| Concentration of human serum albumin (mg/ml) | Before heating: Number of colonies per 0.1 ml | Before heating: Virus infection | After heating: Number of colonies per 0.1 ml | After heating: Virus infection | Recovery of biological activity (%) |
|---|---|---|---|---|---|
| 200 | 116 | Yes | 128 | No | 110.3 |
| 100 | 124 | Yes | 134 | No | 108.1 |
| 20 | 118 | Yes | 51 | No | 43.2 |
| 0 (Control) | 121 | Yes | 0 | No | 0 |

As shown in Table 8, after the heat treatment at 60° C. for 10 hours, viral infectivity was completely lost in every sample, whether albumin had been added or not. This fact indicates that other viruses can also be inactivated by the heat treatment according to this invention. It was found that the biological activity of HGI-glycoprotein was retained in the samples containing albumin, confirming that the addition of albumin is significantly effective.

The results of heat treatment under different conditions were similar to those mentioned above.

In the next experiment, pH of the aqueous solution of the HGI-glycoprotein containing albumin was varied to examine the change in biological activity after heat treatment.

TEST 6

The same HGI-glycopotein as used in Test 5 was dissolved in water to prepare an aqueous solution of 20 mg/ml. To the solution was added 100 mg/ml of human serum albumin (Sigma Co.). The solution covering the pH range 2 to 10 were prepared at 1 unit intervals following manner; pH 2–6, 0.1 M citric acid-sodium phosphate buffer, pH 7 to 10, 0.1 M tris-HCl buffer. Each sample was heated at 60° C. for 10 hours and the remaining biological activity was assayed in the same manner as in Test 5. The ratio (in %) of the number of colonies formed after heat treatment to that before heat treatment was referred to as recovery of biological activity. The results obtained were as shown in Table 9. The biological activity of the HGI-glycoprotein was remarkably retained in the pH range of 5 to 9, indicating that the adjustment of pH of the HGI-glycoprotein solution to this range is necessary before heat reatment.

TABLE 9

| pH | Number of colonies per 0.1 ml | Recovery of biological activity |
|---|---|---|
| Before heat treatment | 86 | 100.0 |
| 2 | 0 | 0 |
| 3 | 0 | 0 |
| 4 | 0 | 0 |
| 5 | 82 | 95.3 |
| 6 | 96 | 111.6 |
| 7 | 118 | 137.2 |
| 8 | 100 | 116.3 |
| 9 | 68 | 79.1 |
| 10 | 0 | 0 |

In another test described later, an aqueous solution containing at least 70 mg/ml of the HGI-glycoprotein was adjusted to pH 2-10 with an acid or alkeli solution and the recovery of biological activity after heat treatment was examined. It was found that the recovery of biological activity was about 40 to 50% at a pH in the range of 5 to 9, whereas the biological activity of an aqueous solution of the HGI-glycoprotein solution of a pH less than 5 or more than 9 has completely disappeared after the heat treatment.

TEST 7

The dependence of the effect of heat treatment on the concentration of the HGI-glycoprotein in aqueous solution was examined.

The purified HGI-glycoprotein analogous to sample No. 6 of Referential Example 1 was dissolved in water and adjusted to pH 7.0 with 0.1 M tris-HCl buffer. The solution was further adjusted to final concentrations of 10, 50, 60, 70, 80, 100, 150 and 200 mg/ml, respectively. Each solution was heated at 60° C. for 10 hours, then cooled immediately in ice water, sterilized by filtration, and lyophilized. The biological activity of each sample was assayed in the same manner as in Test 5. The results obtained were as shown in Table 10.

TABLE 10

| Concentration of HGI-glycoprotein (mg/ml) | Number of colonies per 0.1 ml | Recovery of biological activity % |
|---|---|---|
| 10 | 0 | 0 |
| 50 | 31 | 25.4 |
| 60 | 35 | 28.2 |
| 70 | 44 | 35.5 |
| 80 | 50 | 40.3 |
| 100 | 51 | 41.1 |
| 150 | 53 | 42.7 |
| 200 | 56 | 45.2 |
| Before heat treatment | 124 | 100.0 |

As is apparent from Table 10, when the concentration of the HGI-glycoprotein is 50 mg/ml, the recovery of biological activity after heat treatment was 25.4%. It was found that in order to recover a biological acitivity of at least 35% after heat treatment, the concentration of the HGI-glycoprotein is necessary at least 70 mg/ml, preferably 100 to 200 mg/ml.

TEST 8

The same HGI-glycoprotein as used in Test 5 was dissolved in water, adjusted to various pH's covering a range of 2 to 10 by the addition of 0.01 M citric acid-sodium phosphate buffer for the pH range of 2 to 6 and 0.1 M tris-HCl buffer for the pH range of 7 to 10 and each solution was adjusted the final concentration to 100 mg/ml with distilled water heated at 60° C. for 10 hours, then cooled immediately in ice water and tested, as in Test 5, for the biological activity after heat treatment. A portion of the above solution (pH 4.5) before the adjustment of pH was used as control. The results obtained were as shown in Table 11.

TABLE 11

| pH | Number of colonies per 0.1 ml | Recovery of biological activity (%) |
|---|---|---|
| Before heat treatment | 136 | 100 |
| 2 | 0 | 0 |
| 3 | 0 | 0 |
| 4 | 0 | 0 |
| 5 | 51 | 37.5 |
| 6 | 54 | 39.7 |
| 7 | 59 | 43.3 |
| 8 | 63 | 46.3 |
| 9 | 49 | 36.0 |
| 10 | 0 | 0 |
| pH not adjusted | 0 | 0 |

As shown in Table 11, when the pH of the HGI-glycoprotein solution was in the range from 5 to 9, the recovery of biological activity was 36.0 to 46.3%. If the pH was below 5 or above 9, the biological activities were found completely lost. From the results of Tests 7 and 8, it was found that in heat-treating the HGI-glycoprotein solution, the concentration of HGI-glycoprotein should be at least 70 mg/ml and pH within the range from 5 to 9.

TEST 9

The procedure of Test 5 was repeated, except that the HGI-glycoportein was dissolved in water in a concentration of 200 mg/ml water; serum albumin was not added, and the solution was adjusted to pH 7.0. After the heat treatment, only the virus infective dose was determined as in Test 5. In the sample, virus activity was found completely lost. The result indicates that other viruses than those used can also be inactivated by the heat treatment according to this invention.

The aforementioned method of virus inactivation by heating with a stabilizer is to be adopted on the HGI-glycoprotein having a certain level of purity. The present inventors, therefore, made effort to establish a practical method which can be employed for the intermediate process of producing purified HGI-glycoprotein. As a result, the present inventors have found that the HGI-glycoprotein solution containing at least 70 mg/ml of a protein originated from the urine used as starting material is a heat-resistant solution suitable for the purpose. This novel method of stabilizing the HGI-glycoprotein solution against heating is described below in detail.

One liter of fresh urine collected from normal humans generally contains 30 to 50 mg of proteins. Such human urinary proteins were concentrated by the known method of ultrafiltration, ion exchange chromatography, adsorption on silica gels, salting out, or a combination of these methods. The urinary proteins including the HGI-glycoprotein were further concentrated in vacuo to adjust the protein content to at least 70 mg/ml, preferably 100 to 150 mg/ml. If the protein content of the HGI-glycoprotein-containing fraction is below 70 mg/ml, the loss in biological activity of the HGI-glycoprotein on heating becomes undesirably large. Although any crude fraction containing 70 mg/ml or more of urinary proteins will suit the purpose, a crude fraction obtained in the aforementioned process for producing the HGI-glycoprotein according to this invention is preferable for the novel stabilizing method. The crude fraction is adjusted to a urinary protein content of at least 70 mg/ml and to pH 5 to 9, preferably pH 6 to 8.

The heat-stabilized HGI-glycoprotein solution thus obtained or, if necessary, after having been purified by the procedure described before, is subjected to heat treatment under the conditions described above to yield a fraction readily used as a medicine or a product having the aforementioned physical and chemical properties.

TEST 10

The procedure of Referential Example 1 was repeated to obtain the HGI-glycoprotein-containing fraction analogous to sample No. 1, except for the following modification:

The precipitate formed by salting out with ammonium sulfate to 70% saturation was divided into 8 portions. Each portion was dissolved in water and adjusted to pH 7.0 with 0.1 M tris-HCl buffer. The eight solutions were adjusted to the final protein content of 10, 50, 60, 70, 80, 100, 150 and 200 mg/ml, respectively. Each solution was further divided into two groups. The one group was heat-treated at 60° C. for 10 hours and the other was unheated. All solution samples were subjected to further purification, as described in Referential Example 1, to the level of sample No. 4 of Referential Example 1. Thus, there were obtained two seris of samples with varied protein content, the one series (test samples) having been heat-treated and the other (control samples) untreated.

Each sample was tested for the biological activity in the same manner as in Test 5. The results obtained were as shown in Table 12.

TABLE 12

|  | Sample No. | Protein content (mg/ml) | Number of colonies per 0.1 ml | Recovery of biological activity (%) |
|---|---|---|---|---|
| Control sample | 1 | 10 | 106 | — |
|  | 2 | 50 | 111 | — |
|  | 3 | 60 | 115 | — |
|  | 4 | 70 | 106 | — |
|  | 5 | 80 | 110 | — |
|  | 6 | 100 | 118 | — |
|  | 7 | 150 | 120 | — |
|  | 8 | 200 | 137 | — |
| Test sample | 9 | 10 | 45 | 42.5 |
|  | 10 | 50 | 89 | 80.2 |
|  | 11 | 60 | 98 | 85.2 |
|  | 12 | 70 | 104 | 98.1 |
|  | 13 | 80 | 109 | 99.1 |
|  | 14 | 100 | 121 | 102.5 |
|  | 15 | 150 | 123 | 102.5 |
|  | 16 | 200 | 141 | 102.9 |

EXAMPLE 1

The procedure of Referential Example 1 was repeated several times to obtain 100 mg of the HGI-glycoprotein corresponding in purity to sample No. 6. To 100 mg of the purified HGI-glycoprotein thus obtained, was added with 100 ml of 10% of human serum protein (Green Cross Co., Japan) as stabilizer. The resulting solution was adjusted to pH 6.8 with 10% sodium hydroxide solution, heated at 60° C. for 10 hours, then quenched immediately in ice water, and sterilized with Millipore filtration system (Millipore Co.) provided with membrane filters of 0.45μ pore size. Each 1 ml of sterilized solution was aceptically filled in 1 ml portions in glass vials which had been sterilized by heating at 180° C. for 2 hours. After lyophilized under aseptic conditions, the vials were hermetically sealed to obtain 97 vials each containing 1 mg of a preparation containing heat-treated HGI-glycoprotein.

The preparations obtained above were tested for the biological activities and viral infectiosities in the same manner as in Test 5. The biological activities were comparable to that of an untreated sample and no viral infective activities were detected.

EXAMPLE 2

One thousand liters of fresh urine collected from normal humans were treated in the same manner as in Referential Example 1. The effluent from the CM Sephadex C-50 ion exchange column was concentrated to 1 liter of the crude HGI-glycoprotein solution. To the crude concentrate was added 10 liters of 0.1 M tris-HCl buffer (pH 7.0), stirred thoroughly and again concentrated to about one-tenth by used of DIAFLO hollow fiber ultrafiltration apparatus. To the concentrate was added 5 liters of 0.1 M tris-HCl buffer (pH 7.0) and 5 liters of DEAE cellulose suspension (300 g DEAE cellulose on dry basis) which had been equilibrated with 0.1 M tris-HCl buffer (pH 7.0). The mixture was stirred for 30 minutes and, after standing, filtered under vacuum to collect the DEAE cellulose. The DEAE cellulose thus obtained was washed by the addition of 10 liters of 0.1 M tris-HCl buffer (pH 7.0). The DEAE cellulose was collected by filtration under vacuum, again washed with 10 liters of 0.1 M tris-HCl buffer containing 0.05 M sodium chloride and filtered under vacuum to collect the DEAE cellulose. To the DEAE cellulose was added 10 liters of 0.1 M tris-HCl buffer (pH 7.0) containing 0.3 M sodium chloride and stirred to elute the HGI-glycoprotein-containing fraction from the DEAE cellulose. The eluate was desalted by use of DIAFLO hollow fiber ultrafiltration apparatus (type DC-30). The desalted fraction was lyophilized to obtain about 15 g of a powder. The powder was dissolved in 150 ml by distilled water and applied to the Sephadex G-150 column (6.0×80 cm), which had been equilibrated with 0.1 M tris-HCl buffer (pH 7.0). The fractions corresponding to Ve/Vo ratios of 1.11–1.60 were collected. The combined fraction was thoroughly dialized against distilled water and the dialized solution was concentrated by use of DIAFLO hollow fiber ultrafiltration apparatus (type DC-2) to obtain 100 ml of a concentrate containing about 3 g of crude HGI-glycoprotein.

The grams of powdered human placental albumin (prepared by the method described in Example of Japanese Patent Publication No. 40,132/76) of 98% purity, as determined by electrophoresis, was dissolved in the concentrate obtained above. The resulting solution was adjusted to pH 6.8 with 10% aqueous sodium hydroxide solution, sterilized by filtration as in Example 1, aseptically filled, in 2.5 ml portions, in vials, lyophilized aseptically, and hermetically sealed to obtain 40 vials of a preparation each containing about 3.8 mg of heat-treated HGI-glycoprotein.

The above preparations were tested for the biological activities and viral infectiosities in the same manner as in Test 5. The biological activities were comparable to that of the preparation not heat-treated and no viral infectiosities was detected.

EXAMPLE 3

Four hundreds liters of fresh urine collected from normal humans was adjusted to pH 8 with 10% sodium hydroxide solution and, while cooling at 10° C., centrifuged by means of a continuous centrifuge running at 15,000 G to remove insolubles. The supernatant was adjusted to pH 7 with 10% hydrochloric acid and passed through a silica gel column (10×80 cm). The substances adsorbed on the silica gel were eluted with 40 liters of 5% ammonium solution. The eluate was adjusted to pH 7.5 with 1 N sulfuric acid and added with ammonium sulfate to 70% saturation, left standing overnight at 0° C., and the precipitate formed was collected by filtration. The precipitate was dissolved in 2 liters of 5% ammonium solution, placed in cellophane tubes (Vishking Co.) and dialyzed thoroughly against 0.05 M phosphate buffer (pH 6.5). The dialyzed solution was made up to 10 liters with the same buffer and passed through the CM Sephadex C-50 ion exchange column (40×40 cm), which had been equilibrated with 0.05 M phosphate buffer (pH 6.5), to remove the impurities by adsorption. Ten liters of the effluent was concentrated by means of DIAFLO hollow fiber ultrafiltration apparatus (Amicon Co., type DC-30) and the concentrate was dialyzed against 0.1 M tris-HCl buffer (pH 7.0) at 5° C. for overnight in a manner similar to that described before.

The dialyzed solution was made up to 1 liter with the same buffer and passed through the DEAE cellulose column (4.0×40 cm) which had been equilibrated with the same buffer. The column was thoroughly washed with 0.1 M tris-HCl buffer (pH 7.0) and then eluted with 0.1 M tris-HCl buffer (pH 7.0) containing 0.3 M sodium chloride. The fractions which were capable of stimulating effect on the proliferation and differentiation by mouse bone marrow cells in vitro, as assayed by the same method as used in Test 5, were collected. The combined fraction was dialyzed against 0.1 M tris-HCl buffer (pH 7.0). The dialyzed solution was again passed through the DEAE cellulose column (4.0×40 cm) which had been equilibrated with the same buffer. The column was eluted by a linear concentration gradient elution of sodium chloride (0 to 0.3 M). The fractions having a stimulating effect on proliferation and differentiation of granulocyte were collected and admixed with ammonium sulfate to 70% saturation. The formed precipitate was collected, dissolved in a small amount of 0.1 M tris-HCl buffer (pH 7.0) and dialyzed against the same buffer.

Twenty milliliters of the dialyzed solution was applied to the Sephadex G-150 column (4.0×60 cm) which had been equilibrated with 0.1 M tris-HCl buffer (pH 7.0) and the effluent fractions obtained at Ve/Vo ratios of 1.11–1.45 were collected. The combined fraction was thoroughly dialyzed against distilled water and the dialized solution was lyophilized to obtain about 500 mg of a powder.

Two hundred milligrams of the above powder was dissolved in 0.02 M phosphate buffer (pH 7.0) containing 1.0 M sodium chloride and passed through a column containing 100 ml of concanavalin A-Sepharose 4B (Fine Chemical Laboratory), which had been equilibrated with the same buffer. The column was thoroughly washed with 0.02 M phosphate buffer (pH 7.0) containing 1.0 M sodium chloride and thereafter eluted with a 0.02 M phosphate buffer (pH 7.0) containing 50 mM α-methyl-D-glucoside and 1.0 M sodium chloride. The fractions which have a stimulating effect on the proliferation and differentiation of granulocyte, as assayed by the method described in Test 5, were collected and dialyzed against distilled water. The dialized solution was lyophilized.

About 50 mg of the lyophilized powder obtained above was dissolved in 1 ml of 0.125 M tris-glycine buffer (pH 6.8) containing 10% glycerine and electrophored at 10 mA under cooling by means of a preparative electrophoresis apparatus (Type Fuji Kabara II of Fuji Riken Co., Japan) employing 8% acrylamide gel (pH 8.9; 20 mm×25 mm). The fraction with a relative mobility of 0.46 was recovered with 0.025 M tris-glycine buffer (pH 8.3), then dialyzed against distilled water and the dialyzed solution was lyophilized to obtain about 10 mg of the HGI-glycoprotein.

The above procedure was repeated a number of times and about 1 g of the HGI-glycoprotein was obtained. One gram of the HGI-glycoprotein thus obtained was completely dissolved in 10 ml of water and adjusted to pH 6.8 with 10% aqueous sodium hydroxide solution. The resulting solution was heated at 60° C. for 10 hours, then quenched in ice water, diluted 10-fold with sterile water and sterilized by filtration with Millipore filtration system (Millipore Co.) provided with membrane filters of 0.45μ pore size. Each 1 ml of the sterilized solution was aseptically filled, in glass vials which had been sterilized by heating at 180° C. for 2 hours. After aseptic lyophilization, the vials were hermetically sealed. There were thus obtained about 97 vials containing each 10 mg of the heat-treated HGI-glycoprotein preparation.

The above preparations were tested for biological activities and viral infectiosities by the same methods as used in Tests 5 and 7. The biological activity was about 40% of that of the preparation before the heat treatment and no viral activity was detected.

EXAMPLE 4

One thousand liters of fresh urine collected from normal humans were treated in a manner similar to that in Example 3 and 2.5 liters of an aqueous solution containing the crude HGI-glycoprotein were obtained from the CM Sephadex C-50 column effluent. To the solution was added 25 liters of 0.1 M tris-HCl buffer (pH 7.0). After thorough stirring, the solution was concentrated to about 1/25 of the initial volume by means of DIAFLO hollow fiber ultrafiltration apparatus. To the concentrate were added, 5 liters of 0.1 M tris-HCl buffer and 5 liters of DEAE cellulose suspension (300 g on dry basis of DEAE cellulose) which had been equilibrated with 0.1 M tris-HCl buffer (pH 7.0). The mixture was stirred for 30 minutes, then left standing, and filtered under vacuum to collect the DEAE cellulose. The collected DEAE cellulose was washed with the addition of 10 liters of 0.1 M tris-HCl buffer (pH 7.0), filtered under vacuum, washed with 0.1 M tris-HCl buffer (pH 7.0) containing 0.05 M sodium chloride and filtered under vacuum. The DEAE cellulose thus treated was stirred in 10 liters of 0.1 M tris-HCl buffer (pH 7.0) containing 0.3 M sodium chloride to elute the HGI-glycoprotein-containing fraction from the DEAE cellulose. The eluate was desalted by using DIAFLO hollow fiber ultrafiltration apparatus (Type DC-30). After lyophilization, about 15 g of a powder were obtained.

The lyophilized powder obtained above was dissolved in 150 ml of distilled water and applied to the Sephadex G-150 column (6.0×80 cm), which had been equilibrated with 0.1 M tris-HCl buffer (pH 7.0). The HGI-glycoprotein-containing fractions obtained at Ve/Vo ratios of 1.11–1.60 were collected and dialized thoroughly against distilled water.

The dialized solution was concentrated by using DIAFLO hollow fiber ultrafiltration apparatus (Type DC-2) to obtain 30 ml of a concentrate containing about 3 g of the crude HGI-glycoprotein. The concentrate was adjusted to pH 6.8 with sodium hydroxide and heat-treated under the same conditions as in Example 3. The heat-treated concentrate was sterilized by filtration and aseptically filled, in 1.0 ml portions, in vials. After aseptic lyophilization, the vials were hermetically sealed. Thus, there were obtained 30 vials containing each 5.2 mg of the heat-treated HGI-glycoprotein preparation.

The above preparations were tested for the biological activities and viral infectiosities by the same method as in Tests 5 and 7. The biological activity was about 40% of that before heat treatment and no viral activity was detected.

EXAMPLE 5

The procedure of Referential Example 1 was repeated to obtain about 500 mg (about 26 mg in terms of active substance) of the HGI-glycoprotein powder corresponding to sample No. 4, except that the following step was included prior to the step of dializing the 5% aqueous ammonia solution of the precipitate obtained on 70% saturation of ammonium sulfate.

About 20 g of the precipitate which was formed was dissolved in water and made up to 200 ml (100 mg/ml protein concentration). The resulting solution was heated at 60° C. for 10 hours and then quenched in ice water to obtain a fraction containing the heat-treated HGI-glycoprotein. This fraction was dialized in the same way as in Example 1. The biological activity of the powdered HGI-glycoprotein obtained was comparable to that of the fraction before the heat treatment and no viral activity was detected.

EXAMPLE 6

About 450 mg of a powder corresponding to sample No. 4 of Referential Example 1 and containing 23.5 mg of HGI-glycoprotein were obtained by repeating the procedure of Referential Example 1, except for the following modification.

Ten liters of the effluent aqueous solution from the CM Sephadex C-50 ion exchange column was concentrated by means of DIAFLO hollow fiber ultrafiltration apparatus to a protein concentration of 70 mg/ml. The concentrated aqueous solution was heated at 60° C. for 10 hours, then quenched in ice water. The insolubles which were formed were removed and the aqueous solution was placed in cellophane tubes (Visking Co.) and dialized against 0.1 M tris-HCl buffer (pH 7.0) at 5° C. The dialized solution was made up to 1 liter with the same buffer to obtain a solution corresponding to sample No. 1 of Referential Example 1.

The biological activity of the HGI-glycoprotein-powder obtained was substantially comparable to that of the powder obtained without the heat treatment. No viral activity was detected.

EXAMPLE 7

About 500 mg of a powder corresponding to sample No. 4 of Referential Example 1 and containing about 26 mg of HGI-glycoprotein were obtained by repeating the procedure of Referential Example 1, except for the following modification.

The precipitate obtained by salting out the effluent from the DEAE cellulose column with ammonium sulfate was dissolved in 0.1 M tris-HCl buffer to a protein content of 150 mg/ml. The resulting solution was heated at 60° C. for 10 hours, and quenched in ice water. After removal of the formed precipitate by filtration, the aqueous solution was dialized against 0.1 M tris-HCl buffer to obtain a dialized solution which was used in place of sample No. 3 in Referential Example 1.

The biological activity of the HGI-glycoprotein-containing powder finally obtained was substantially comparable to the preparatiion obtained without heat treatment. No viral activity was detected.

EXAMPLE 8

Fifty liters of fresh urine collected from normal humans were neutralized with a 10% sodium hydroxide solution and centrifuged by means of a continuous centrifuge with cooling device and running at 10,000 G. The supernatant was immediately concentrated ten-fold by means of DIAFLO hollow fiber ultrafiltration apparatus (Aminon Co., type DC-30 provided with a molar weight cut-off 10,000 membrane). After addition of 50 liters of water, the solution was again concentrated to obtain 3 liters of concentrate. The concentrated urine was further concentrated by means of a rotary vacuum evaporator to obtain about 50 ml of concentrate having a protein content of 70 mg/ml. The concentrate was heated at 60°±0.5° C. for 10 hours and quickly cooled to obtain the heat-treated HGI-glycoprotein-containing fraction. After removal of insolubles which were formed, the concentrate was made up to 5 liters with 0.1 M tris-HCl buffer (pH 7.0) and passed through the DEAE cellulose column (4.0×40 cm), which had been equilibrated with 0.1 M tris-HCl buffer, to allow the HGI-glycoprotein to be adsorbed on the DEAE cellulose. The column was thoroughly washed with 0.1 M tris-HCl buffer (pH 7.0) and eluted with 0.1 M tris-HCl buffer (pH 7.0) containing 0.3 M sodium chloride. Thereafter, the procedure of Referential Example 1 was repeated, except that the eluate obtained above was used in place of the 5% aqueous ammonia solution of the precipitate obtained on 70% saturation with ammonium sulfate. There were thus obtained about 200 g of the HGI-glycoprotein powder corresponding to sample No. 4 by repeating the procedure of Referential Example 1.

The biological activity of the finally obtained HGI-glycoprotein powder was substantially comparable to that of the preparation obtained without the heat treatment. No viral activity was detected.

EXAMPLE 9

The procedure of Referential Example 1 was repeated to collect the fraction corresponding to sample No. 3 of Referential Example 1. The fraction was concentrated to a protein content of 70 mg/ml and heated at 60° C. for 10 hours. Thereafter, the fraction was quenched in ice water, freed from the formed precipitate and treated in the same manner as in Referential Example 1 to obtain about 10 mg of a HGI-glycoprotein powder corresponding to sample No. 6 of Referential Example 1.

The biological activity of the finally obtained HGI-glycoprotein powder was substantially comparable to that of the preparation without heat treatment.

What is claimed is:

1. A virus-inactivated glycoprotein from human urine which stimulates human bone marrow cells to form colonies of granulocytes and which has the following physical and chemical properties:
   (a) molecular weight: 75,000 to 90,000 dalton as determined by gel filtration;
   (b) solubility: soluble in water, slightly soluble in chloroform, and insoluble in ethyl alcohol and acetone;
   (c) specific optical rotation: $[\alpha]_D^{20} = 0 \pm 40$ (0.25% aqueous solution);
   (d) pH: 5.0–6.0 (1% by weight aqueous solution);
   (e) isoelectric point: pH $4.7 \pm 0.2$;
   (f) thermostability: on being heated at $60° \pm 0.5°$ C. for 30 minutes in 1% aqueous solution, the stimulating function on the proliferation and differentiation of the human granulocyte is completely lost;
   (g) electrophoresis: the relative mobility is 0.25 in the electrophoresis using sodium dodecyl sulfate-polyacrylamide gel;
   (h) infrared absorption: characteristic absorption at the following wave numbers ($cm^{-1}$): 3600–3200 (strong absorption), 1700–1600 (strong absorption), 1550 (medium absorption), 1430–1380 (medium absorption), and 1150–1000 (broad band);
   (i) color reaction: colors characteristic of saccharides are produced by the $\alpha$-naphthol-sulfuric acid reaction, indole-sulfuric acid reaction, anthrone-sulfuric acid reaction and phenol-sulfuric acid reaction; colors characteristic of polypeptide linkage and amino acids are produced by the Lowry-Folin's reaction and by the ninhydrin reaction after hydrolysis with hydrochloric acid;
   (j) constituent amino acids of the protein moiety: proline, aspartic acid, threonine, serine, glutamic acid, glycine, alanine, valine, methionine, isoleucine, leucine, tyrosine, phenylalanine, lysine, histidine, tryptophan and arginine;
   (k) color and shape: substantially white and amorphous;
   (l) sugar composition of the polysaccharide moiety: 10.0–13.0% by weight in terms of glucose of neutral sugars, 3.0–7.0% by weight of sialic acids and 1% by weight of other amino sugars;
   (m) weight ratio of protein to polysaccharide: 75–85: 13.0–20.0; and
   (n) elementary analysis: 42.3–47.3% of carbon, 5.7–7.8% of hydrogen, 9.6–14.3% of nitrogen, 34.4–39.4% of oxygen and 0.2% or less of sulfur.

2. A therapeutic agent for leukopenia containing as active material a glycoprotein according to claim 1.

3. A therapeutic agent for leukopenia containing as active material a glycoprotein according to claim 1 having a specific biological activity of 35,000 units/mg or more.

4. A process for producing a virus-inactivated glycoprotein which stimulates human bone marrow cells to form colonies of granulocytes, which comprises concentrating urine with of normal humans respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material collecting fractions of a relative effluent of 1.11 to 1.60, adjusting the aqueous solution containing the collected fractions to pH 5–9, and heating the resulting aqueous solution at 50°–70° C. for 8–30 hours in the presence of albumin of the human origin to inactivate viruses.

5. A process according to claim 4, wherein the concentration of albumin in the aqueous solution is 2.0% (W/V) or more.

6. A process according to claim 4, wherein the albumin originates from human serum or human placenta.

7. A process for producing a virus-inactivated glycoprotein which stimulates human bone marrow cells to form colonies of granulocytes, which comprises concentrating human urine with respect to proteins contained therein, contacting the urinary proteins with a cation exchanger to remove impurities by adsorption on said exchanger, contacting the effluent with an anion exchanger to adsorb the active material, eluting the active material with a saline silution according to linear concentration gradient elution, subjecting the eluate to gel filtration chromatography on a highly crosslinked polymer gel to develop the active material collecting fractions of a relative effluent of 1.11 to 1.60, subjecting the collected fractions to affinity chromatography with a sugar affinitive absorbent to adsorb the effective ingredient, eluting the adsorbed active material with a 20–100 mM saccharide solution, adjusting the aqueous solution containing the collected fractions to pH 5–9, and heating the resulting aqueous solution at 50°–70° C. for 8–30 hours in the presence of albumin of the human origin to inactivate viruses.

8. A process according to claim 7, wherein the concentration of albumin in the aqueous solution is 2.0% (W/V) or more.

9. A process according to claim 7, wherein the albumin originates from human serum or human placenta.

10. A process for producing a virus-inactivated glycoprotein which stimulates human bone marrow cells to form colonies of granulocytes, which comprises concentrating human urine with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to absorb the active material, eluting the adsorbed active material with a 20–100 mM saccharide solution, subjecting the eluate to preparative zone electrophoresis, eluting the active material with a salt solution, adjusting the eluate to pH 5–9, and heating the resulting eluate at 50°–70° C. for 8–30 hours in the presence of albumin of the human origin to inactivate viruses.

11. A process according to claim 10, wherein the concentration of albumin in the aqueous solution is 2.0% (W/V) or more.

12. A process according to claim 10, wherein the albumin originates from human serum or human placenta.

13. A process for producing a virus-inactivated glycoprotein which stimulates human bone marrow cells to form colonies of granulocytes, which comprises concentrating human urine with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to absorb the active material, eluting the adsorbed active material with a 20–100 mM saccharide solution, subjecting the eluate to preparative zone electrophoresis, eluating the active material with saline solution, adjusting the concentration of active material in the eluate to at least 70 mg/ml and the pH to 5–9, and heating the resulting eluate at 50°–70° C. for 8–30 hours to inactivate viruses.

14. A process according to claim 13, wherein the concentration of active material in the final heat treatment step is 100–200 mg/ml.

15. A process for producing a virus-inactivated glycoprotein which stimulates human bone marrow cells to form colonies of granulocytes, which comprises concentrating human urine with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, and collecting fractions of a relative effluent of 1.11 to 1.60; the active material containing fraction including the concentrated human urine with respect to urinary proteins in any of the above steps being subjected to virus inactivating treatment by heating the fraction in the form of aqueous solution at 50°–70° C. for 8–30 hours under such conditions that the protein content of the aqueous solution has been adjusted to at least 70 mg/ml and the pH to 5–9.

16. A process according to claim 15, wherein the protein content of the aqueous solution is 100–150 mg/ml.

17. A process for producing a virus-inactivated glycoprotein which stimulates human bone marrow cells to form colonies of granulocytes, which comprises concentrating human urine with respect to proteins contained therein, contacting the urinary proteins with a cation exchanger to remove impurities by adsorption on said exchanger, contacting the effluent with an anion exchanger to absorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, and eluting the adsorbed active material with a 20–100 mM saccharide solution, the active material containing fraction including the concentrated human urine with respect to urinary protein in any of the above steps being subjected to virus inactivating treatment by heating the fraction in the form of aqueous solution at 50°–70° C. for 8–30 hours under such conditions that the protein content of the aqueous solution has been adjusted to at least 70 mg/ml and the pH 5–9.

18. A process according to claim 17, wherein the protein content of the aqueous solution is 100–150 mg/ml.

19. A process for producing a virus-inactivated glycoprotein which stimulates human bone marrow cells to form colonies of granulocytes, which comprises concentrating human urine with respect to proteins contained therein, contacting the slurry proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, eluting the adsorbed active material with a 20–100 mM saccharide solution, subjecting the eluate to preparative zone electrophoresis, and eluating the active material with a saline solution to recover the active material in pure form; the active material containing fraction including the concentrated human urine with respect to urinary protein in any of the above steps being subjected to virus inactivating treatment by heating the fraction in the form of aqueous solution at 50°–70° C. for 8–30 hours under such conditions that the protein content of the aqueous solution has been adjusted to at least 70 mg/ml and the pH to 5–9.

20. A process according to claim 19, wherein the protein content of the aqueous solution is 100–150 mg/ml.

21. A process for stimulating human bone marrow cells to form colonies of granulocytes comprising supplying to the bone marrow an amount of the glycoprotein of claim 1 effective to increase the colonies of granulocytes.

* * * * *